United States Patent [19]

Jakubowicz

[11] 4,424,191

[45] Jan. 3, 1984

[54] ANALYZER FEATURING LOADING AND UNLOADING MEANS FOR A STORAGE CHAMBER, AND COMMON DRIVE MEANS

[75] Inventor: Raymond F. Jakubowicz, Rush, N.Y.

[73] Assignee: Eastman Kodak Company, Rochester, N.Y.

[21] Appl. No.: 354,859

[22] Filed: Mar. 4, 1982

[51] Int. Cl.³ ............................................. G01N 35/04
[52] U.S. Cl. ........................................ 422/65; 422/63
[58] Field of Search ....................... 436/63, 64, 65, 66

[56] References Cited

U.S. PATENT DOCUMENTS

| | | | |
|---|---|---|---|
| 3,955,930 | 5/1976 | Shapiro | 422/50 |
| 4,142,656 | 3/1979 | Smith et al. | 222/325 |
| 4,152,390 | 5/1979 | Nosco et al. | 422/63 |
| 4,269,803 | 5/1981 | Jessop | 422/63 |
| 4,296,069 | 10/1981 | Smith et al. | 422/65 X |
| 4,298,571 | 11/1981 | DiFulvio et al. | 422/65 |
| 4,302,420 | 11/1981 | Jakubowicz et al. | 422/63 |
| 4,303,611 | 12/1981 | Jessop | 422/63 X |
| 4,321,122 | 3/1982 | Whitcomb et al. | 422/63 X |

*Primary Examiner*—Arnold Turk
*Attorney, Agent, or Firm*—Dana M. Schmidt

[57] ABSTRACT

An analyzer comprising a storage chamber, means for loading and unloading test elements into the storage chamber by first and second members, respectively, and a reversible drive means. The storage chamber is constructed to receive more than one such test element. The drive means is continuously coupled to both the first and second members so as to effect simultaneous movement of the two members relative to the storage chamber, but without simultaneously loading and unloading the storage chamber by said movement of said members.

10 Claims, 6 Drawing Figures

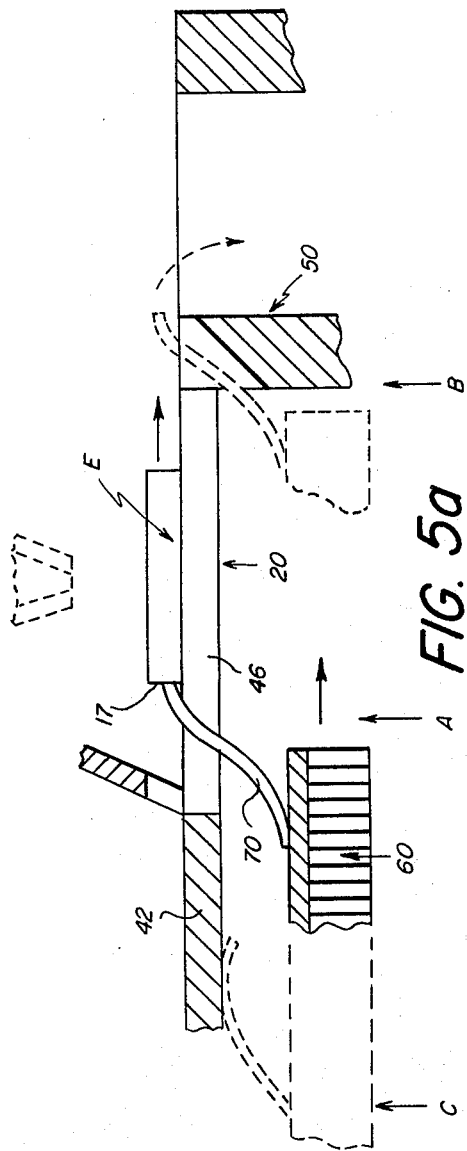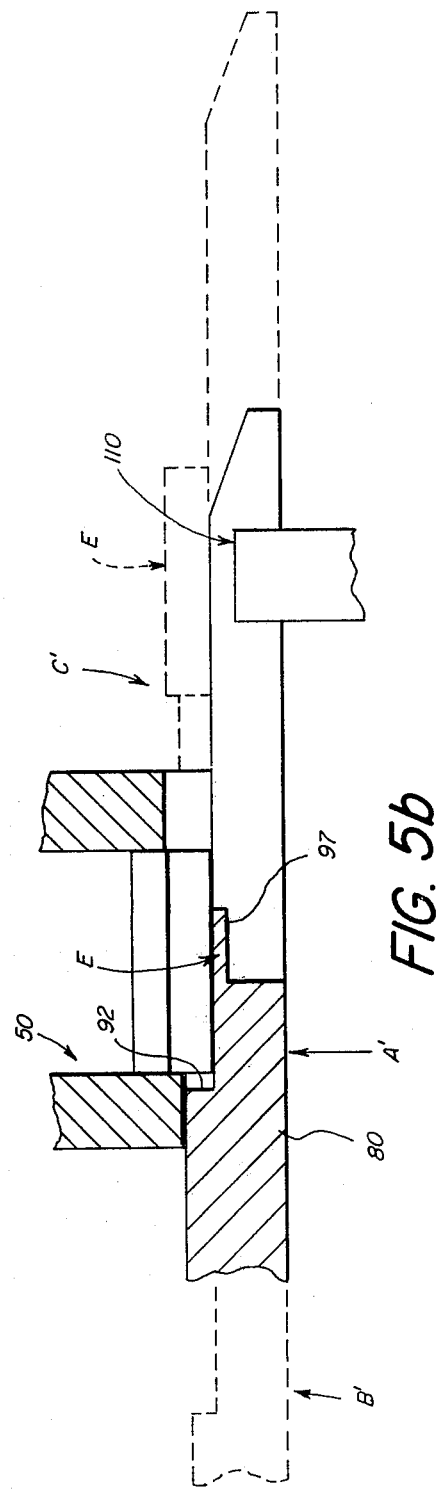

ANALYZER FEATURING LOADING AND UNLOADING MEANS FOR A STORAGE CHAMBER, AND COMMON DRIVE MEANS

FIELD OF THE INVENTION

This invention relates to apparatus for the chemical analysis of substances, known as analytes, in liquids.

BACKGROUND OF THE INVENTION

Commonly owned U.S. application Ser. No. 177,050, filed on Aug. 11, 1980, now U.S. Pat. No. 4,303,611 by T. Jessop entitled "Analyzer Apparatus Featuring a Simplified Incubator", describes a unique analyzer and incubator for the same wherein the incubator provides a path from a loading station to an unloading station such that test elements are supported along the path with most of the elements covered by the element adjacent to them. A preferred arrangement is one in which the test elements are incubated as a vertical stack. Such an arrangement has produced a greatly simplified analyzer and at the same time has prevented loss of gases from the test elements. As a result, analyzers are readily available for use in small offices that could not afford to purchase the large and complicated prior art analyzers that have been so characteristic of the field.

Notwithstanding the significant advantages provided by the invention described in the aforesaid application, there has been an interest in further simplifying the analyzer. For example, the preferred loading and unloading means of the invention described in that application involve two separately actuated pusher members. The arrangement of those members is such that a single driving means does not operate to directly actuate both of them. Although a single drive means continuously coupled to both members would tend to simplify the drive mechanisms, the use of such a single drive and continuous coupling would tend to cause the loading means and unloading means to act to simultaneously load one test element into the incubator while another is being unloaded therefrom. However, the incubators of the aforesaid application are designed to contain more than one test element. Simultaneous loading and unloading of such an incubator is undesirable because, with such an arrangement, there could never be more than one test element in the incubator at any one time. To avoid this, separate control of the loading and unloading functions is required.

Thus, prior to this invention, it was not envisoned to provide, in simplified analyzer-incubator apparatus of the type described in the aforesaid application, a drive means continuously coupled to both the loading and unloading means of the multi-element incubator.

SUMMARY OF THE INVENTION

The present invention provides a simplified analyzer wherein a single drive means is continuously coupled to members that separately load and unload a multi-element storage (e.g., incubation) chamber. The continuous coupling is achieved by providing for each member to move to an idle position when the other member is loading or unloading the storage chamber.

More specifically, in accord with one aspect of the invention, there is provided an analyzer having a metering station, a storage station (e.g., an incubator station) including a storage chamber constructed to store more than one test element; a detection station including a detector for detecting a change in the test elements; and means for moving such test elements into and out of the metering station, storage chamber and the detector. The analyzer is improved in that the moving means include first and second members constructed to move between first, second and third positions relative to the storage chamber, and a reversible drive means for these members. Only movement of the members between the second and third positions is effective to load and unload respectively, the test elements into and out of the storage chamber. The first position is the idle position. The drive means is coupled to both the first and second members so as to synchronously move the two members relative to the storage chamber, only one of the members at a time being moved from the second to the third position.

In accord with a further aspect of the invention, notwithstanding such simultaneous movement of the two members, movement of one of the members is one direction effects movement of a test element either into, or out of the storage chamber, but not both.

Thus, it is an advantage of the present invention that an analyzer of the type described in the aforesaid application has a single drive means simultaneously driving both the loading and unloading means in a manner such that the loading and unloading functions nevertheless occur independently.

Other features and advantages will become apparent upon reference to the following Description of the Preferred Embodiments, when read in light of the attached drawings.

BRIEF DESCRIPTION OF THE DRAWINGS

FIGS. 5a–5b are enlarged section views similar to that of FIG. 2, illustrating the sequence of the steps in the operation of the analyzer of the invention.

DESCRIPTION OF THE PREFERRED EMBODIMENTS

The specific embodiments hereinafter described refer to an analyzer having an incubator wherein most of the test elements cover the next adjacent element, preferably in a stack, and detection station means comprising a fiber optics reflectometer. In addition, the invention is applicable to an analyzer using any kind of storage chamber adapted to contain more than one test element. Further, it is applicable to an analyzer using any detector means for detecting properties of the test element, whether it be a reflectometer for measuring an optical density change, a fluorimeter for measuring fluorescence or phosphorescence in the test element, or some other kind of detector.

The analyzer of this invention is capable of measuring a variety of analytes of liquids, particularly those of biological liquids. This is accomplished preferably through the use of generally flat test elements E, FIG. 2, that feature one or more liquid-containing portions mounted in a plastic frame member 15. The liquid-containing portions are mounted on a transparent, liquidimpervious support. The liquid is applied by depositing a quantity, such as a drop, onto the test element.

Edges 16 and 17 define the leading and trailing edges, respectively, of the elements as they are moved into the analyzer.

The layers of the test elements preferably are constructed in the manner described in, for example, U.S. Pat. No. 3,992,158, issued Nov. 16, 1976, and Re 30,267, reissued May 6, 1980, the details of which are expressly incorporated herein by reference. Deposited sample liquid spreads into the layers where the reaction takes place that generates a detectable change. U.S. Pat. No. 4,169,751, issued on Oct. 2, 1979, discloses one useful form of such a test element wherein the sample-receiving portion is staked to a support frame apertured to receive a liquid drop. The disclosed details of the element of the last-named patent are incorporated herein by reference.

The invention hereinafter described refers to blood serum as the preferred liquid under analysis. In addition, other analyte-containing liquids are so analyzable, including industrial liquids containing nonbiological analytes.

Figure 1:
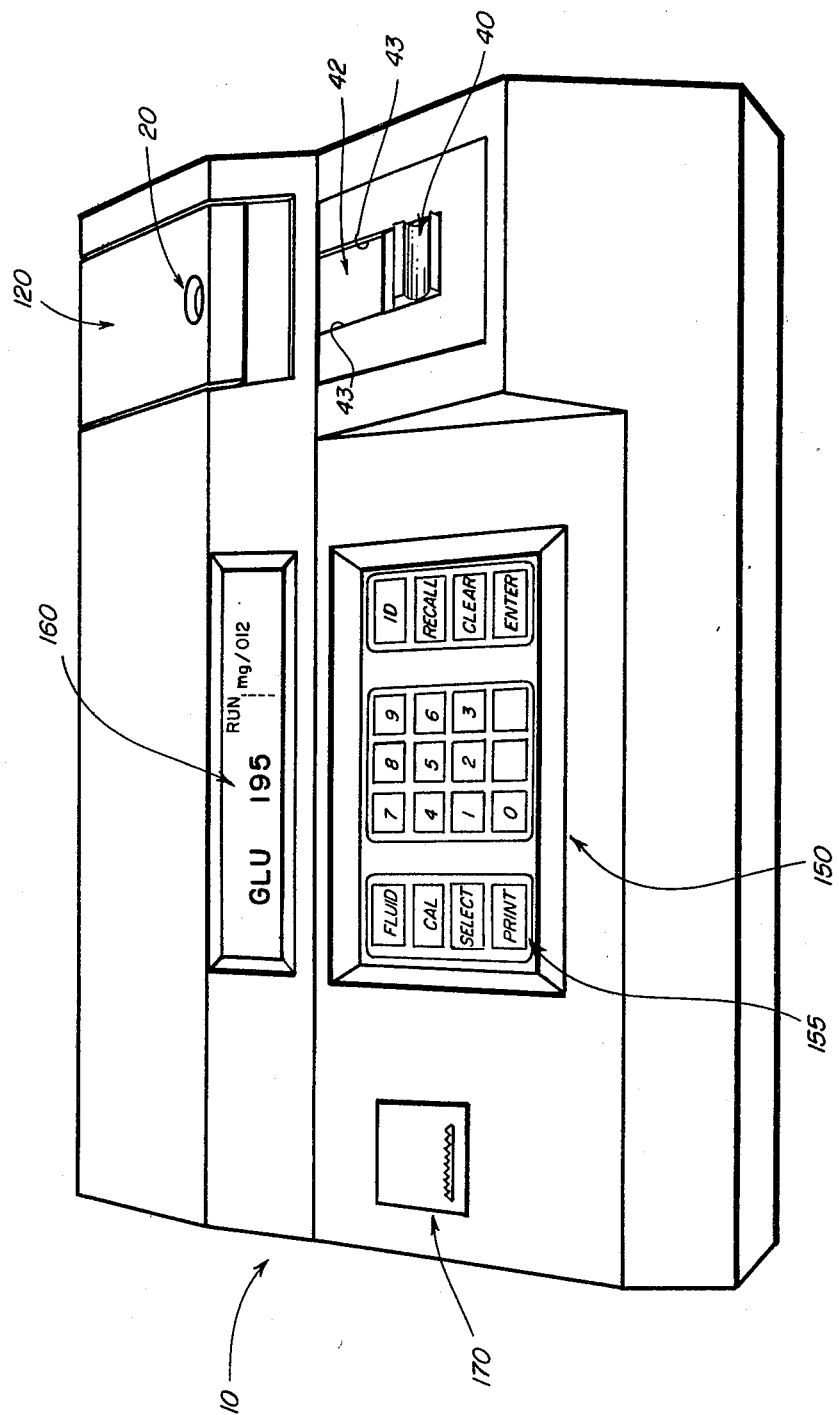
FIG. 1 is an isometric view of an analyzer prepared in accordance with the invention.
Figure 2:
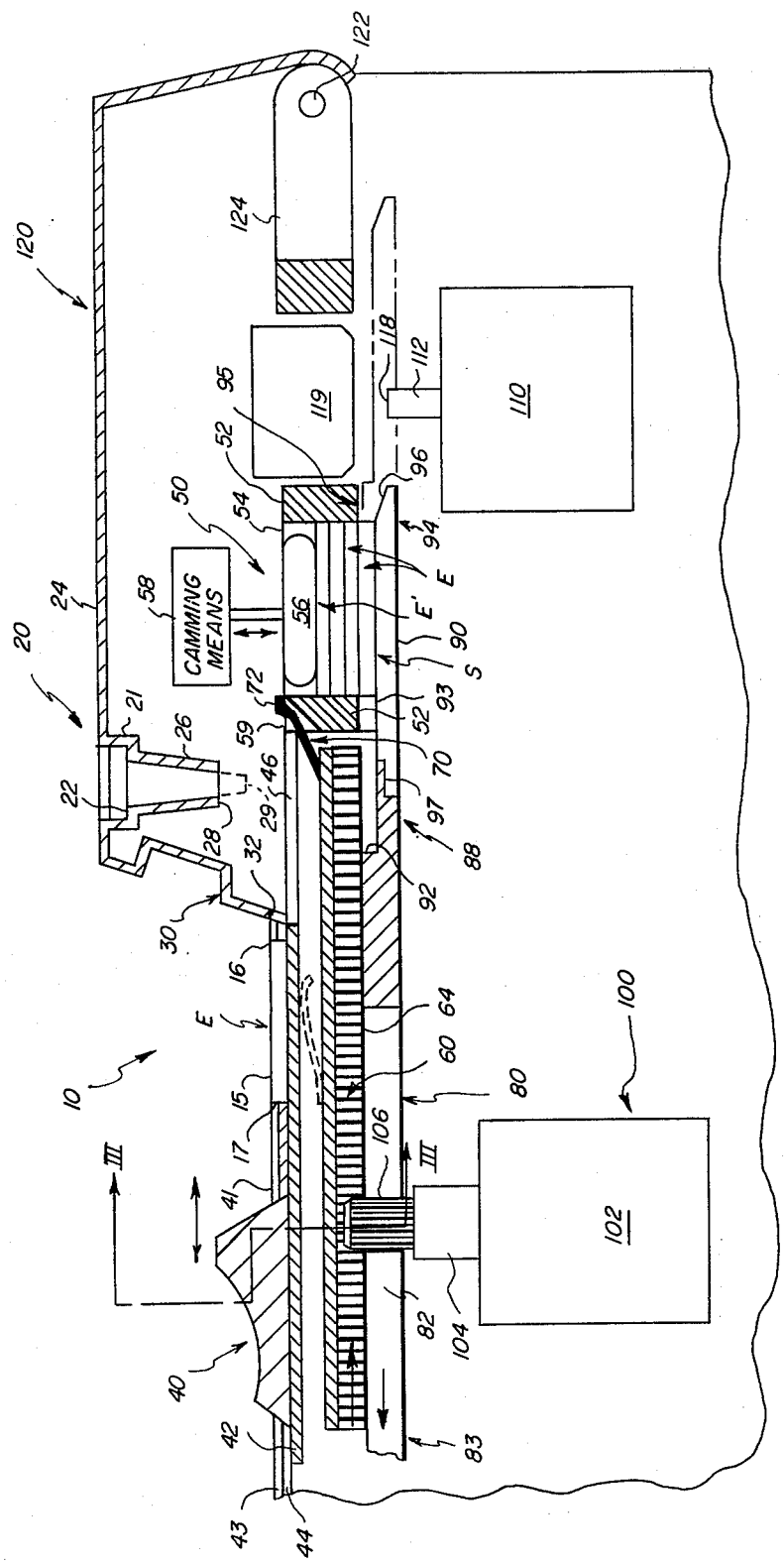
FIG. 2 is a fragmentary elevational view, in section, taken generally through the metering station at the right-hand portion of the apparatus of FIG. 1.

An analyzer 10 constructed in accordance with this invention includes, FIGS. 1 and 2, a metering station 20, a storage station comprising a storage chamber or incubator 50, means 40 for moving test element E to the station 20, a detection station 110 containing a reflectometer, and test element moving or transport means. The moving or transport means include means 60 for loading a test element E into chamber 50, unloading means 80 for unloading an element from the chamber, and drive means 100 for driving the loading and unloading means 60 and 80. Optionally a pivotable cover 120 is included, enclosing the portions that are preferably operated under controlled conditions. Cover 120 is preferably hinged at 122 to a bracket 124.

As shown, FIG. 2, metering station 20 is a molded portion of cover 120 shaped to accommodate a conventional pipette, not shown. A portion 21 projects inwardly from the exterior surface 24 of cover 120 to form a shoulder 22 which terminates in a truncated cone 26 that is apertured at 28. Cone 26 and aperture 28 are sized to align and support the tip 29 of the pipette, so that a quantity of liquid can be dispensed therefrom.

Figure 3:
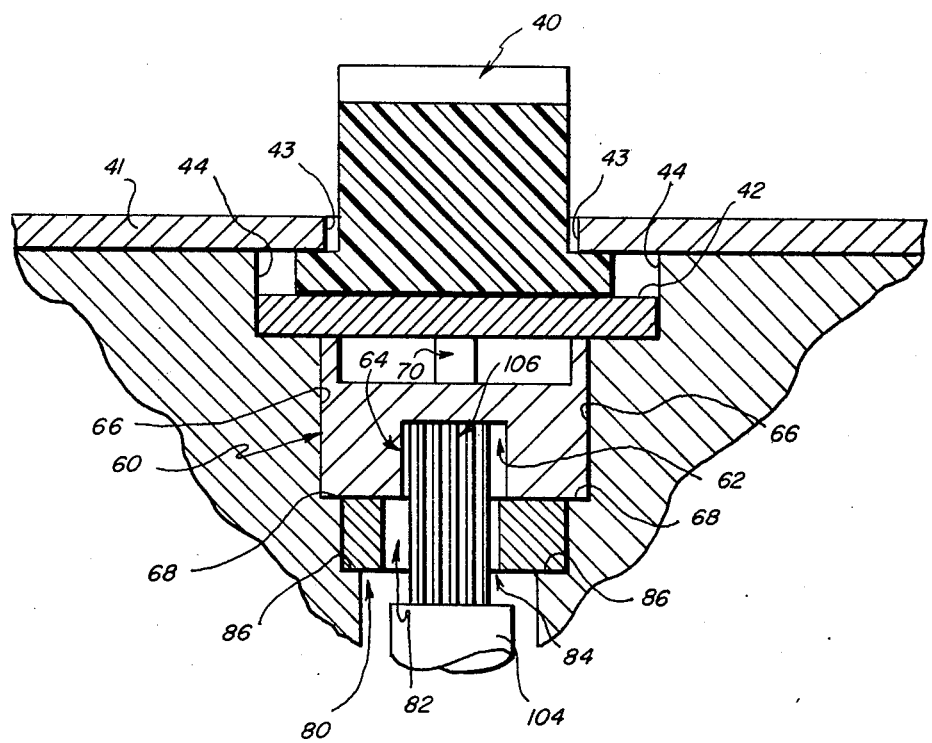
FIG. 3 is a section view taken generally along the line III—III of FIG. 2.

To permit a test element E to be pushed into station 20 through cover 120, the cover includes at front portions 30 thereof, a slot 32 sized to permit passage of such a test element. The test element is moved through the slot preferably by means of slide 40 that is mounted for manual reciprocation between a cover plate 41 and a support plate 42, FIG. 3. Edge surfaces 43 of plate 41 are spaced apart to allow slide 40 to reciprocate between them. Support plate 42 is mounted between two linear and parallel shoulders 44. The portion of plate 42 that extends under front portion 30 of cover 120 at slot 32 is slotted in locations 46 extending generally parallel to shoulders 44. Slot 46 permits loading member 60, discussed hereinafter, to engage test elements located at metering station 20.

Disposed further within cover 120, adjacent to station 20 and preferably collinear with the path traveled by slide 40 between edge surfaces 43, is the storage chamber or incubator 50, hereinafter simply "incubator". This incubator is preferably constructed in the manner described in the aforesaid U.S. application Ser. No. 177,050 entitled "Analyzer Apparatus Featuring a Simplified Incubator", the details of which are expressly incorporated herein by reference. More specifically, incubator 50 comprises vertically extending opposed pairs of walls 52 and 54, a weighted cover 56, and camming means 58 adapted to raise cover 56 when a test element E is advanced past station 20 towards incubator 50. The upper portion of first wall 52 is provided with a slot 59 that accommodates finger 70 of loading member 60 when member 60 reaches the edge of incubator 50 in its most advanced position (solid lines, FIG. 2). The walls 52 and 54 are dimensioned to receive test elements E in a stack S such that each covers and contacts the test element below it, except for the uppermost element E' which is covered by cover 56. Conventional heating elements, not shown are preferably included in walls 52 and/or 54 to maintain the temperature of the incubator at a desired level.

To load a test element E into incubator 50 from metering station 20, a first member 60 is provided, mounted under support surface 42 for reciprocal movement. Member 60 is preferably centrally notched at 62, FIG. 3, along the length of its bottom surface, and one wall of the notch is provided with a rack gear 64, FIGS. 2 and 3. Member 60 reciprocates within a passage provided by opposed surfaces 66 and supporting shoulders 68, FIG. 3.

Member 60 further includes, at its end proximal to metering station 20, a flexible finger 70, FIG. 2, that is spring-biased to project upwardly into the plane of the path of movement of test elements into and out of metering station 20. Slots 46 and 59 are disposed to accommodate this extension of finger 70. Tip 72 of finger 70 is curved to provide a camming surface that allows finger 70 to bend back under support surface 42 when member 60 is retracted to its most rearward, or idle, position C, shown in dotted lines, FIG. 5A. The flexibility of finger 70 also permits a test element to override the finger and enter metering station 20, when member 60 occupies position A.

To unload a test element E from the bottom of the stack S on a first-in, first-out basis, a second member 80 is provided, mounted under first member 60 for reciprocal movement, FIG. 2. Member 80 is also notched lengthwise, at 82, FIGS. 2 and 3, at least at end portion 83 thereof distal to incubator 50. One wall of notch 82 is provided with a rack gear 84. However, gear 84 is provided along the notch wall that is opposite to the notch wall bearing gear 64 of member 60, thereby insuring that the two members are reversely coupled to gear 106. The support for second member 80 is provided by shoulders 86, such that members 60 and 80 are constrained to move along parallel paths, in a common plane, one above the other.

End portion 88, FIG. 2, of member 80 that is proximal to incubator 50 is adapted to remove the bottommost element E from stack S. For this purpose, end portion 88 is provided with bifurcated arms 90 and a raised shoulder 92 adapted to engage such bottommost element, in the manner described in commonly owned U.S. application Ser. No. 223,559, now U.S. Pat. No. 4,302,420, filed on Jan. 9, 1981, by Raymond F. Jakubowicz, entitled "Analyzer Featuring a Contacting Reflectometer". The content of that application is expressly incorporated herein by reference. Slot 93 is provided in first wall 52 to allow arms 90 and shoulder 92, but not a test element E, to pass therethrough. (See FIG. 5b.) Second wall 52 has a larger slot 95 that allows passage of arms 92 and the test elements. A lip 97 extends between arms 90, under the position occupied by test elements E carried by member 80, and the undersurface of lip 97 is preferably provided with white and dark reference coatings for detector 110.

Forward movement of shoulder 92 towards detector 110 serves to advance the test element under weight 119 at detector 110, described hereinafter. During retraction of shoulder 92 to the position B' shown in dotted lines, FIG. 5b (solid lines in FIG. 2), retaining springs, not shown, prevent rearward movement of the advanced test element at the detector. Ends 94 of arms 90 are provided with a camming surface 96 adapted to raise test elements off detector 110 before sliding them relative to the detector, as described in the aforesaid Jakubowicz application. This action by camming surface 96 preserves the detector from unnecessary wear.

First and second members 60 and 80 are continuously coupled to the common drive means 100, FIG. 2, for simultaneous movement. As used herein, a "continuous coupling" refers to a coupling that produces movement in both members 60 and 80 when drive means 100 moves, without any provision for disengagement. That is, the coupling of the drive means is preferably continuous to avoid the necessity for means for disengaging the coupling when one member is not actively moving a test element along its path. The movement of members 60 and 80 is between positions A, B and C and A', B', and C', respectively, FIGS. 5a and 5b. Drive means 100 comprises a motor 102, a rotatable drive shaft 104, and preferably a pinion gear 106 mounted on shaft 104, FIG. 2. Gear 106 is continuously coupled to or engaged with both rack gears 64 and 84, FIG. 3. Any reversible motor 102 is useful, for example, a stepper motor such as the motor manufactured by Airpex. In addition, other gear configurations are permitted for gears 64, 84 and 106, it being preferred that members 60 and 80 remain reversely coupled.

Figure 4:
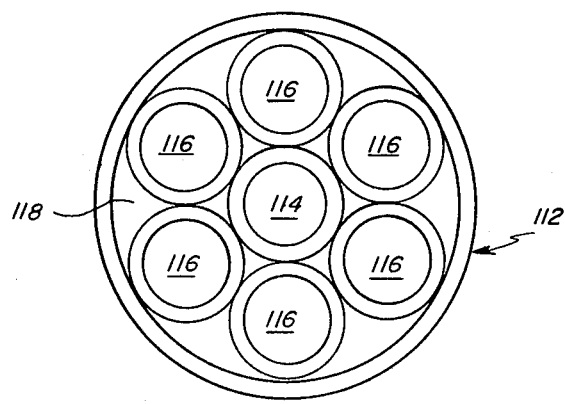
FIG. 4 is a plan view of the exposed face of the fiber optics reflectometer that contacts the test element.

Disposed still further within cover 24, adjacent to incubator 50 and preferably aligned with the incubator and metering station 20, is detector 110. Most preferably, detector 110 is a fiber optics reflectometer, such as a detector constructed in the manner described in the aforesaid Jakubowicz application. In such a detector, a fiber optics head 112 is provided with at least one conventional light-emitting fiber 114, FIG. 4. A plurality of conventional light-collecting fibers 116 are bonded together as a coparallel bundle forming a face 118 at which the light is emitted and collected, respectively. Face 118 is flat as shown in FIG. 2, or slightly convexly curved. Weight 119 forces a properly positioned test element into contact with face 118. The under-surface of weight 119 is preferably provided with a black coating. Detector 110 preferably includes at least one light-emitting diode connected to fiber 114 and a silicon p.i.n. photodetector and conventional amplification circuitry not shown, connected to fibers 116.

Alternatively, detector 110 comprises a head 112 wherein the fiber optics comprise a large number of smaller diameter fibers, not shown, more than one of which is light-emitting.

The advancement of the test elements through the above-described stations is preferably done automatically, following the metering of the liquid at station 20. The devices useful for such automatic control include sensors, switches, and a microprocessor, not shown, all of which are conventional devices. Display of the analyte concentration is achieved by conventional display devices, for example, a liquid crystal display 160 and/or a thermal printer 170, FIG. 1.

The operation of analyzer 10 will be readily apparent from the preceding description. A test element E is placed on plate 42 in front of slide 40, as shown in FIG. 2. Manual operation of slide 40 serves to push the test element under the pipette that is held at metering station 20. The analyte for which that test element is constructed is either keyed into the microprocessor by using a command key 155 of keyboard 150, FIG. 1, or, preferably, appropriate code markings on test element E are automatically sensed and recorded in the microprocessor. The liquid sample is metered into the test element at station 20, and either an additional command is keyed into the analyte by keyboard 150 that metering is complete, or a sensor automatically generates that command. The subsequent sequence of movement of members 60 and 80 is best illustrated in FIGS. 5a and 5b. To move a test element out of metering station 20, motor 102 is automatically activated to move member 60 to bring finger 70 to the position A, FIG. 5a. In this position, finger 70 engages trailing edge 17 of the test element. When member 60 is moved in this fashion, motor 102 also moves member 80 so that shoulder 92 is in the position A', FIG. 5b, at which, if moved forward, member 80 would engage a test element E in incubator 50. Motor 102 is then activated to advance member 60 so that finger 70 is in position B shown in phantom, FIG. 5a. Camming means 58 raises cover 56 during this movement, so that incubator 50 is loaded with the test element. Simultaneously, member 80 is moved rearwardly by motor 102 to its idle position B', FIG. 5b.

Meanwhile, the microprocessor times the residence of all test elements in incubator 50. When the timing sequence dictates that the bottommost element is to be unloaded, motor 102 is reversed, causing member 60 and finger 70 to be withdrawn from position B, FIG. 5a. Finger 70 passes through position A and retreats to its idle position C shown in phantom. At the same time, member 80 advances from position B', FIG. 5b, passes through position A' to engage and unload test element E from incubator 50, and moves to position C' shown in phantom, FIG. 5b. In this position, shoulder 92 is effective to transfer the unloaded test element into detector 110, and to permit a reference reading to be taken of the coatings on lip 97. The test element previously at detector 110 is pushed out by the advancing test element.

After lower member 80 is withdrawn to position A' from the position C' shown in phantom, FIG. 2, the transferred test element is read by detector 110. The withdrawal of member 80 to position A' also acts to advance finger 70 from position C to position A, where it is in position to engage the next test element that is pushed into metering station 20.

It will be apparent, therefore, that as upper member 60 is advancing to load elements E into incubator 50, lower member 80 is withdrawing in a manner that leaves undisturbed the elements in stack S. When lower member 80 advances to unload stack S, upper member 60 withdraws without disturbing test elements not yet in stack S. Only one of the members moves at a time through the positions at which it engages a test element to load it into, or unload it from, the incubator.

After the last test element is detected, it remains at detection 110 until eventually a new test element ejects it.

The density reading obtained by detector 110 is converted by suitable, conventional programming of the microprocessor into a concentration reading. The concentration is displayed, for example, by display 160 and printer 170.

The materials used to make the parts described above are not critical, metals and plastics being the preferred choices. Parts that are to convey heat, such as walls 52, 54 and cover 56, are preferably formed from metals.

Other arrangements are also useful as embodiments of the invention. For example, one useful arrangement features an integral connection between the loading and unloading members, not shown, so that they both move together in the same direction when the drive means is actuated.

The invention has been described in detail with particular reference to preferred embodiments thereof, but it will be understood that variations and modifications can be effected within the spirit and scope of the invention.

What is claimed is:

1. In an analyzer for the chemical analysis of a liquid contained in a test element, the analyzer comprising
   metering station means at which liquid is deposited onto such a test element;
   storage station means comprising a storage chamber constructed to store more than one such test element, said chamber having one end disposed for loading such elements and an opposite end disposed for unloading said stored elements from said chamber;
   detection station means for detecting a change in said unloaded test elements; and
   means for sequentially moving each of such test elements into said metering station means, from said metering station means into said chamber, and from said chamber into said detection station means;
   the improvement wherein said moving means include:
   (a) a first member movable along a first path between: (1) an idle position upstream of said metering station means, (2) an element-engaging position at said metering station means, and (3) an element loading position at said one end of said storage chamber;
   (b) a second member movable along a second path spaced from said first path, between: (1) an idle position upstream of said storage chamber, (2) an element-engaging position at said opposite end of said storage chamber, and (3) an element loading position at said detection station means;
   and reversible drive means coupled to said first member and said second member for sequentially moving said first member to its (1), (2) and (3) positions while synchronously moving said second member respectively to its (3), (2) and (1) positions, and vice versa;
   whereby said drive means is effective to operate both said movable members without disengagements and without simultaneous loading and unloading of said storage chamber.

2. An analyzer as defined in claim 1, wherein said first and second members are reversely coupled to said drive means so that actuation of said drive means effects opposite relative simultaneous movement of said members.

3. An analyzer as defined in claim 2, wherein said members are constrained to move along parallel paths.

4. An analyzer as defined in claim 3, wherein said paths lie in a common plane, one generally above the other.

5. An analyzer as defined in claim 1 or 2, wherein said drive means includes a rotatable gear and each of said members includes a rack gear engaged by said rotatable gear.

6. In an analyzer for the chemical analysis of a liquid contained in a test element, the analyzer comprising
   metering station means permitting liquid to be deposited onto such a test element;
   an incubator constructed to incubate more than one such test element, said incubator having one end disposed for loading such elements and an opposite end disposed for unloading said stored elements from said incubator;
   detection station means comprising a detector for detecting a change in said unloaded test elements;
   and means for sequentially moving each of such test elements into said metering station means, from said metering station means into said incubator, and from said incubator into and out of said detection station means;
   the improvement wherein said moving means include:
   (a) a first member movable along a first path between: (1) an idle position upstream of said metering station, (2) an element-engaging position at said metering station, and (3) an element loading position at said incubator;
   (b) a second member movable along a second path spaced from said first path, between: (1) an idle position upstream of said incubator, (2) an element-engaging position at said incubator, and (3) an element loading position at said detector;
   and reversible drive means continuously coupled to both said first member and said second member to simultaneously move said members relative to said incubator and between said positions (1), (2), and (3);
   said first and second members being disposed relative to said incubator and said drive means such that said drive means moves one of said members between its positions (1) and (2) while it moves the other of said members between its positions (2) and (3).

7. An analyzer as defined in claim 6, wherein said first and second members are reversely coupled to said drive means so that actuation of said drive means effects opposite relative simultaneous movement of said members.

8. An analyzer as defined in claim 7, wherein said members are constrained to move along parallel paths.

9. An analyzer as defined in claim 6, 7, or 8, wherein said drive means includes a rotatable gear and each of said members includes a rack gear engaged by said rotatable gear.

10. In an analyzer for the chemical analysis of a liquid contained in a test element, the analyzer comprising
    metering station means permitting liquid to be deposited onto such a test element;
    storage station means comprising a storage chamber constructed to store more than one such test element, said chamber having one end disposed for loading such elements and an opposite end disposed for unloading said stored elements from said chamber;
    detection station means comprising a detector for detecting a change in said unloaded test element;
    and means for sequentially transporting each of such test elements into said metering station means, from said metering station means into said chamber, and from said chamber into and out of said detection station means;

the improvement wherein said moving means include:

(a) a first member movable along a first path between: (1) an idle position upstream of said metering station, (2) an element-engaging position at said metering station, and (3) an element loading position at said storage chamber;

(b) a second member movable along a second path spaced from said first path, between: (1) an idle position upstream of said storage chamber, (2) an element-engaging position at said storage chamber, and (3) an element loading position at said detector;

and means for moving (a) said first member from its position (2) to position (3) while moving said second member from its position (2) to position (1), and (b) said first member from its position (3) to position (2) and then position (1) while moving said second member from its position (1) to position (2) and then position (3);

said moving means including reversible drive means continuously coupled to both said first and said second members so that only one of said members at a time is capable of moving from its position (2) to position (3).

* * * * *